(12) United States Patent
Ikeda (10) Patent No.: US 9,619,880 B2
(45) Date of Patent: Apr. 11, 2017

(54) MEDICAL DIAGNOSTIC IMAGE PROCESSING APPARATUS

(71) Applicant: Toshiba Medical Systems Corporation, Otawara-shi (JP)

(72) Inventor: Yoshihiro Ikeda, Sakura (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 288 days.

(21) Appl. No.: 14/189,568

(22) Filed: Feb. 25, 2014

(65) Prior Publication Data

US 2014/0233814 A1    Aug. 21, 2014

Related U.S. Application Data

(63) Continuation of application No. PCT/JP2013/073591, filed on Sep. 2, 2013.

(30) Foreign Application Priority Data

Aug. 31, 2012 (JP) ................................. 2012-191619
Sep. 2, 2013 (JP) ................................. 2013-181696

(51) Int. Cl.
  *G06K 9/00*  (2006.01)
  *G06T 7/00*  (2017.01)
  (Continued)

(52) U.S. Cl.
  CPC ............ *G06T 7/0012* (2013.01); *A61B 6/504* (2013.01); *A61B 6/507* (2013.01); *A61B 6/5217* (2013.01); *A61B 6/032* (2013.01)

(58) Field of Classification Search
  None
  See application file for complete search history.

(56) References Cited

U.S. PATENT DOCUMENTS

2005/0065432 A1*  3/2005  Kimura ................ A61B 5/0263
                                                         600/420
2006/0004279 A1*  1/2006  Ikeda ...................... A61B 6/507
                                                         600/411

(Continued)

FOREIGN PATENT DOCUMENTS

CN      102415898 A    4/2012
CN      102651997 A    8/2012

(Continued)

OTHER PUBLICATIONS

International Search Report mailed Dec. 3, 2013 for PCT/JP2013/073591 filed Sep. 2, 2013 with English Translation of Categories.

(Continued)

*Primary Examiner* — Sean Conner
(74) *Attorney, Agent, or Firm* — Oblon, McClelland, Maier & Neustadt, L.L.P.

(57) ABSTRACT

The invention improves the quality of image diagnosis by a user. An image processing unit compares each pixel value of a perfusion image with a threshold, and extracts a lesion candidate region as a collateral circulation candidate or bypass blood vessel candidate from the perfusion image based on a comparison result. The image processing unit displays the lesion candidate region together with a blood vessel image representing the spatial distribution of blood vessels in a head.

13 Claims, 11 Drawing Sheets

(51) Int. Cl.
*A61B 6/00* (2006.01)
*A61B 6/03* (2006.01)

(56) References Cited

U.S. PATENT DOCUMENTS

| | | | |
|---|---|---|---|
| 2007/0098134 A1 | 5/2007 | Toyoshima et al. | |
| 2010/0067767 A1 | 3/2010 | Arakita et al. | |
| 2010/0274119 A1* | 10/2010 | Kabasawa | A61B 5/0263 600/420 |
| 2011/0150309 A1* | 6/2011 | Barfett | G06T 7/0028 382/131 |
| 2012/0063663 A1* | 3/2012 | Kawasaki | G06T 7/0014 382/133 |
| 2012/0238888 A1* | 9/2012 | Bredno | A61B 5/02028 600/504 |

FOREIGN PATENT DOCUMENTS

| | | |
|---|---|---|
| JP | 2007-144139 A | 6/2007 |
| JP | 2010-068958 A | 4/2010 |
| JP | 2012-081254 A | 4/2012 |
| WO | WO 2011/070467 A1 | 6/2011 |

OTHER PUBLICATIONS

International Written Opinion mailed Dec. 3, 2013 for PCT/JP2013/073591 filed Sep. 2, 2013.
International Search Report issued Dec. 3, 2013 in PCT/JP2013/073591 (English translation only).
Combined Chinese Office Action and Search Report issued Jun. 11, 2015 in Patent Application No. 201380001544.3 (with English translation of categories of cited documents).

* cited by examiner

MEDICAL DIAGNOSTIC IMAGE PROCESSING APPARATUS

CROSS-REFERENCE TO RELATED APPLICATIONS

This application is a Continuation Application of PCT Application No. PCT/JP2013/073591, filed Sep. 2, 2013 and based upon and claims the benefit of priority from the Japanese Patent Application No. 2012-191619, filed Aug. 31, 2012 and the Japanese Patent Application No. 2013-181696, filed Sep. 2, 2013, the entire contents of all of which are incorporated herein by reference.

FIELD

Embodiments described herein relate generally to a medical diagnostic image processing apparatus.

BACKGROUND

In head perfusion imaging in an X-ray computed tomography apparatus, blood vessel images of a head are obtained in a time-series in addition to a perfusion image of the head. The user can readily find a collateral circulation caused by angiostenosis or the like by observing the time-series blood vessel images of the head.

There has been a technique of calculating a delay time for each pixel of a portion to be examined using, as a reference time, a time when a contrast agent reaches a specific portion of a brain, and generating an image (to be referred to as a delay image hereinafter) representing the spatial distribution of the delay times (see, for example, patent literature 1). The delay time is defined by, for example, the difference between the earliest time when the blood vessels of the brain start to dye with a contrast agent and the time when the blood vessels of an arbitrary portion of the brain start to dye with the contrast agent.

There is also provided a technique of generating an image (to be referred to as a TTP image hereinafter) which represents the two-dimensional distribution of times (TTPs: time to peak) when a CT value reflecting the existing ratio of a contrast agent in blood vessels becomes largest after the contrast agent flows into a specific portion to be examined.

If time-series blood vessel images of a head are used, it is difficult to find a collateral circulation because it depends on image observation by the user.

The present invention has as its object to provide a medical diagnostic image processing apparatus capable of improving the quality of image diagnosis by the user.

DETAILED DESCRIPTION

In general, according to one embodiment, a medical diagnostic image processing apparatus includes a lesion candidate region extraction unit and a display unit. The lesion candidate region extraction unit compares each pixel value of a perfusion image with a threshold, and extract, based on a comparison result, a lesion candidate region as a collateral circulation candidate or a bypass blood vessel candidate from the perfusion image. The display unit displays the lesion candidate region together with a blood vessel image representing a spatial distribution of blood vessels in a head.

A medical diagnostic image processing apparatus according to an embodiment will be described below with reference to the accompanying drawings. Note that in the following explanation, the same reference numerals denote constituent elements having almost the same functions and arrangements, and a repetitive explanation will be made only when necessary. Note also that a medical diagnostic image processing apparatus according to the embodiment is applicable to any of an X-ray computed tomography apparatus, nuclear magnetic resonance imaging apparatus, and work station. In the following description, a medical diagnostic image processing apparatus will be exemplified as an X-ray computed tomography apparatus.

Figure 1A:
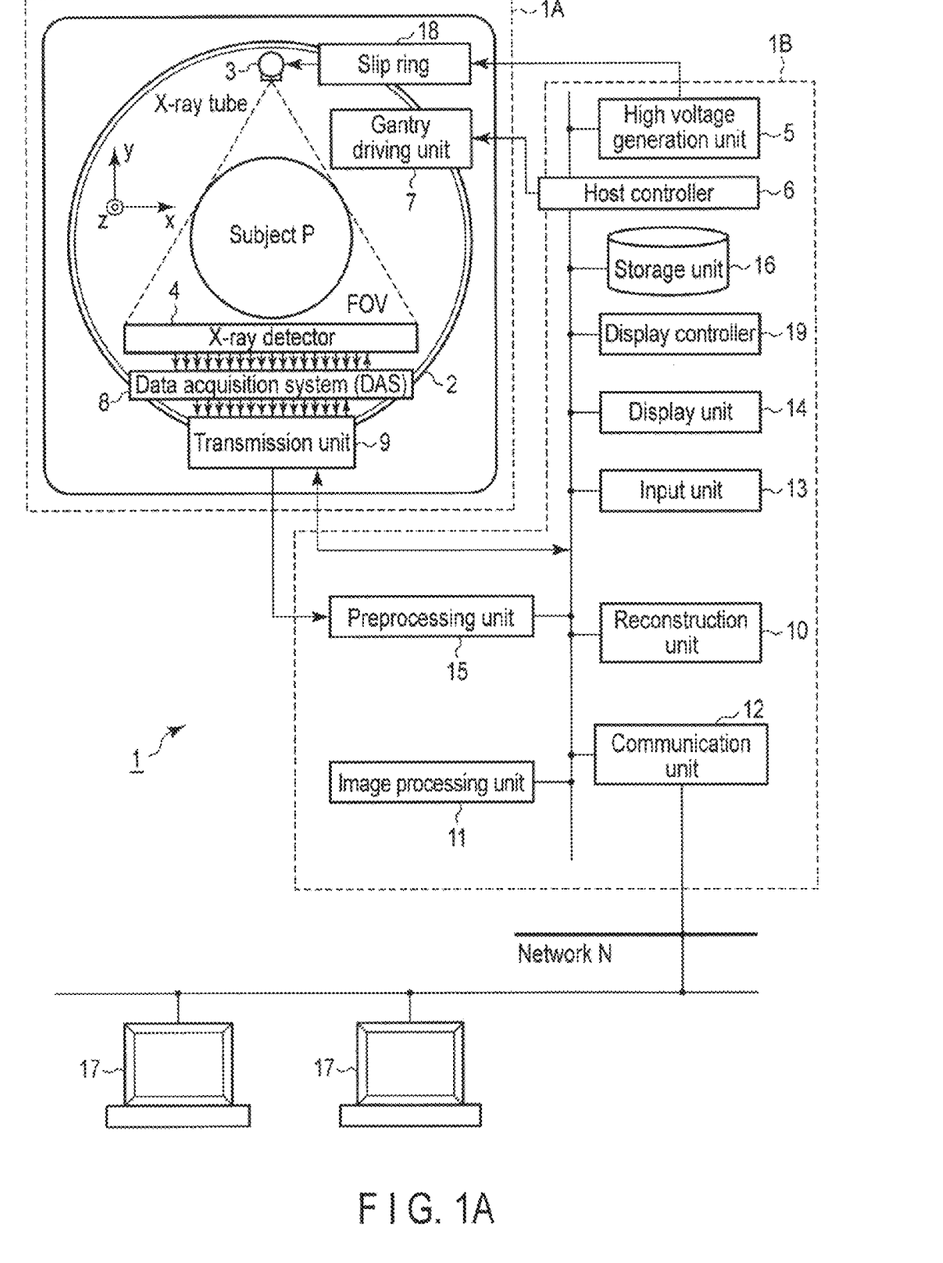
FIG. 1A is a view showing the arrangement of a medical diagnostic image processing apparatus according to an embodiment.

FIG. 1A is a view showing the arrangement of an X-ray computed tomography apparatus 1 according to the embodiment. As shown in FIG. 1A, the X-ray computed tomography apparatus 1 includes a rotating frame 2, X-ray tube 3, X-ray detector 4, high voltage generation unit 5, host controller 6, gantry driving unit 7, data acquisition system (DAS) 8, non-contact data transmission unit 9, volume data reconstruction unit 10, image processing unit 11, network communication unit 12, input unit 13, display unit 14, preprocessing unit 15, storage unit 16, and slip ring 18. The X-ray computed tomography apparatus 1 is connected to workstations 17 via a network.

The X-ray computed tomography apparatus 1 includes a gantry. The gantry rotatably supports the annular or disk-like rotating frame 2. The X-ray tube 3 and the X-ray detector 4 are mounted on the rotating frame 2 to face each other through a subject placed on the top in an imaging region. If the X-ray detector 4 is of a multi-slice type, it includes a plurality of detection element arrays, each including a plurality of channels in the channel direction (X-axis), in the slice direction (Z-axis). If the X-ray detector 4 is of a two-dimensional array type, it includes a plurality of X ray detection elements densely distributed in both the channel direction (X-axis) and the slice direction (Z-direction). The X-ray tube 3 is a vacuum tube which generates X-rays. The high voltage generation unit 5 supplies power (a tube current and a tube voltage) necessary for the emission of X-rays to the X-ray tube 3 via the slip ring 18. Note that the high voltage generation unit 5 may also be mounted on the rotating frame 2, and may directly supply power to the X-ray tube 3. The high voltage generation unit 5 applies a high voltage to the X-ray tube 3 via the slip ring 18 in accordance with instruction information from the host controller 6.

The host controller 6 includes a CPU (Central Processing Unit) and a memory (neither of which is shown). The host controller 6 controls the operations of the high voltage generation unit 5 and the gantry driving unit 7 in accordance with instructions from the input unit 13 to execute a CT scan for an imaging portion of the subject. Controlling the high voltage generation unit 5 makes the rotating frame 2 continuously rotate at a constant angular velocity and makes the X-ray tube 3 generate X-rays continuously or at predetermined angular intervals. The gantry driving unit 7 can drive the top holding mechanism under the control of the host controller 6. Assume that the imaging portion according to the embodiment is a head.

The data acquisition system 8 (DAS) is connected to the X-ray detector 4. The data acquisition system 8 converts a current signal in each channel of the X-ray detector 4 into a voltage, amplifies the voltage, and converts the amplified voltage into a digital signal. The data (raw data) acquired by the data acquisition system 8 is sent to the preprocessing unit 15 via the non-contact type or slip ring type transmission unit 9 using light or magnetism.

The preprocessing unit 15 performs preprocessing such as correction of sensitivity nonuniformity between channels for the raw data and correction of an extreme decrease in signal intensity or signal loss due to an X-ray absorber, mainly a metal portion, with respect to the raw data. Data corrected by the preprocessing unit 15 is called projection data. The reconstruction unit 10 generates a plurality of volume data files (time-series volume data files) at different imaging times based on the projection data. Note that a volume data file from which blood vessels imaged with a contrast agent are extracted will be referred to as a blood vessel volume data file.

The image processing unit 11 analyzes blood flow dynamics in the time-series volume data files, and generates a function image (to be referred to as a perfusion image hereinafter) indicating the spatial distribution of blood flow dynamic indices. The image processing unit 11 extracts a lesion candidate region by performing image processing according to the embodiment for the perfusion image. Furthermore, the image processing unit 11 displays the lesion candidate region in a clinically advantageous form by using the blood vessel volume data file. The lesion candidate region according to the embodiment includes a lesion blood vessel candidate and a cerebral parenchyma region nutrified by the lesion blood vessel candidate. Examples of a lesion blood vessel are a collateral circulation and bypass blood vessel. The collateral circulation is a blood vessel spontaneously generated to compensate for retarded blood flow of a narrowed blood vessel. The bypass blood vessel is a blood vessel surgically formed by revascularization. A representative example of revascularization is an STA-MCA (superficial temporal artery-middle cerebral artery) anastomosis. The STA-MCA anastomosis is a technique of surgically connecting the superficial temporal artery to the middle cerebral artery to compensate for a decrease in blood flow of the middle cerebral artery due to narrowing or the like. The blood vessel connected to the middle cerebral artery is called a bypass blood vessel.

Figure 1B:
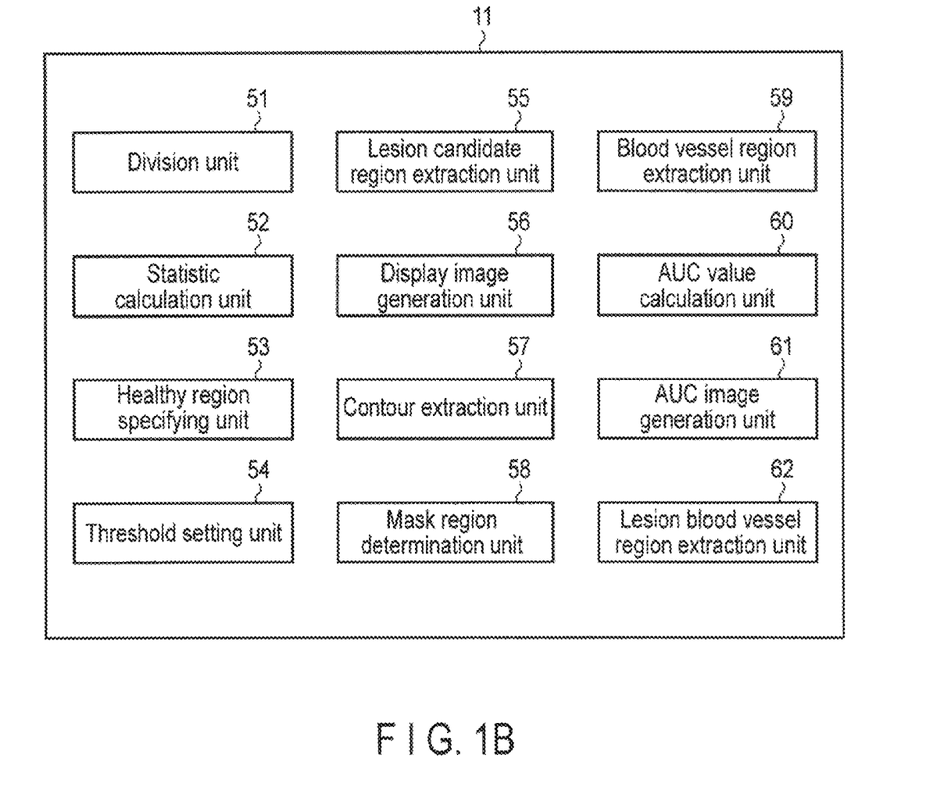
FIG. 1B is a block diagram showing the arrangement of an image processing unit shown in FIG. 1A in more detail.

The image processing unit 11 functionally includes a division unit 51, statistic calculation unit 52, healthy region specifying unit 53, threshold setting unit 54, lesion candidate region extraction unit 55, display image generation unit 56, contour extraction unit 57, mask region determination unit 58, blood vessel region extraction unit 59, AUC value calculation unit 60, AUC image generation unit 61, and lesion blood vessel region extraction unit 62 for, for example, extracting and displaying a lesion candidate region according to the embodiment. The operation of each unit of the image processing unit 11 will be described later.

When a user such as a doctor or a technician inputs a command via the input unit 13, the host controller 6 executes a program stored in the memory. The input unit 13 includes, for example, a main console and a system console. The communication unit 12 performs communication control corresponding to each protocol. The communication unit 12 has a function capable of connecting to a PACS (Picture Archiving and Communication Systems) or the like via an electric communication line such as a telephone line. The storage unit 16 stores various data such as display images and various blood vessel volume data files including volume data. The storage unit 16 stores a perfusion image.

A perfusion image according to the embodiment will be described. As described above, the perfusion image is a function image indicating the spatial distribution of blood flow dynamic indices. A TTP value or delay time is known as a blood flow dynamic index.

Figure 5:
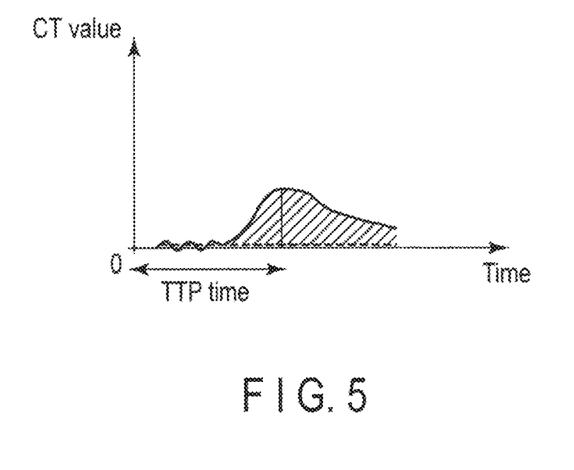
FIG. 5 is a timing chart showing a general example of an AUC according to the embodiment.

FIG. 5 is a timing chart for explaining a TTP value, which shows a change in CT value of a blood vessel portion with time in the time-series volume data files regarding the head injected with a contrast agent. In the timing chart shown in FIG. 5, the ordinate represents the CT value and the abscissa represents time. A reference time 0 indicates a time when the contrast agent reaches the blood vessel portion. As shown in FIG. 5, the CT value of an arbitrary blood vessel portion of the head changes depending on the flow rate of the contrast agent. The flow rate of the contrast agent reaches its peak value at the peak of the CT value. The time from the reference time until the CT value reaches its peak value is called a TTP (time to peak) time. A TTP image 21 shown in FIG. 3A indicates the spatial distribution of TTP values.

A delay time indicates a time difference from when the contrast agent reaches a reference blood vessel portion of the head until the contrast agent reaches each blood vessel portion of the head. A delay image shown in FIG. 3B indicates the spatial distribution of delay times.

The medical diagnostic image processing apparatus according to the embodiment extracts a lesion candidate region from a perfusion image, and displays the extracted lesion candidate region in various layouts. Examples 1 to 4 of the embodiment will be described below.

EXAMPLE 1

Figure 2A:
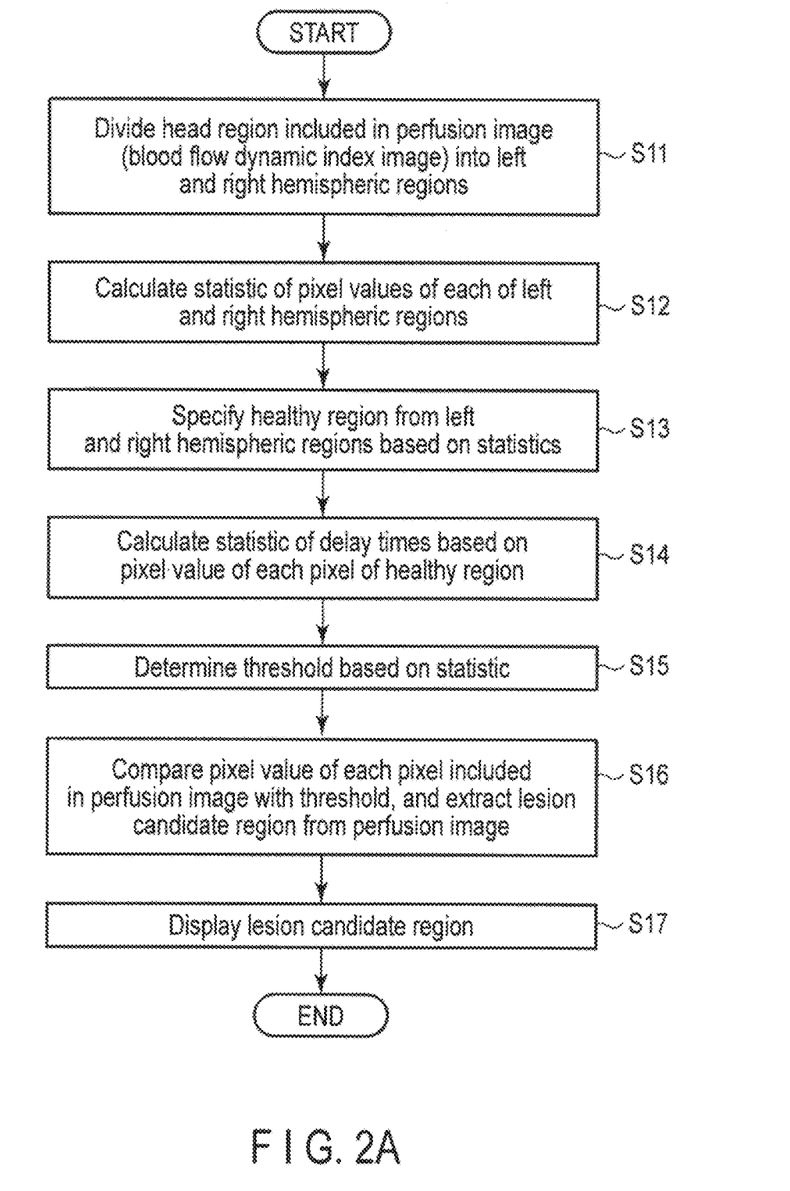
FIG. 2A is a flowchart illustrating a typical processing procedure according to Example 1 of the embodiment.
Figure 3A:
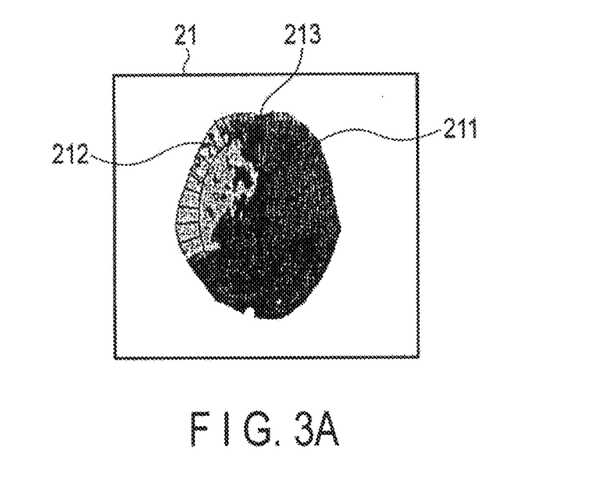
FIG. 3A is a view showing an example of a TTP image according to the embodiment.

FIG. 2A is a flowchart illustrating the typical procedure of lesion candidate region display processing performed under the control of a host controller 6. More specifically, the lesion candidate region display processing is processing from extraction of a lesion candidate region from a healthy region in a perfusion image up to display of an image. First, an image processing unit 11 reads out a perfusion image from a storage unit 16. A division unit 51 of the image processing unit 11 divides a head region included in the readout perfusion image into a plurality of partial regions (step S11). As an example, as shown in FIG. 3A, the division unit 51 sets a center line 213 in a TTP image, sets an image region indicating the left hemisphere with respect to the center line 213 as a left hemispheric region, and sets an image region indicating the right hemisphere with respect to the center line 213 as a right hemispheric region. The center line 213 is set or adjusted by the user via an input unit 13.

A statistic calculation unit 52 of the image processing unit 11 calculates the statistic of pixel values for each of the left and right hemispheric regions (step S12). More specifically, the statistic calculation unit 52 calculates the statistic of pixel values (TTP values) for each of the left and right hemispheric regions of the TTP image. Examples of the statistic are the average value and standard deviation of the TTP values. As shown in FIG. 3A, for example, the statistic calculation unit 52 calculates the average value of the TTP values in a 2-cm region (brain cortex region) outside an intracerebral region in the TTP image separately for each of the left and right hemispheric regions. Note that the statistic may be calculated using either a delay image or a TTP image.

A healthy region specifying unit 53 of the image processing unit 11 specifies a healthy region from the left and right hemispheric regions based on the statistics calculated in step S12 (step S13). For example, the healthy region specifying unit specifies a healthy region based on the average value of the TTP values. The healthy region specifying unit 53 specifies, as a healthy region 211, one of the left and right hemispheric regions which has a smaller average value of the TTP values, and specifies, as a lesion hemispheric region 212, the other region which has a higher average value of the TTP values. Note that the healthy region is not necessarily one of the left and right hemispheric regions. For example, a cerebellar region may be set as a healthy region.

The statistic calculation unit 52 of the image processing unit 11 calculates the statistic of the delay times based on the pixel values of the respective pixels of the healthy region specified in step S13 (step S14). The healthy region may be the healthy region of the TTP image or that of the delay image. For example, the statistic calculation unit 52 calculates the average value and standard deviation of the delay times for a healthy region 222 of the delay image shown in FIG. 3B. Similarly to the delay image, for the TTP image, the statistic calculation unit 52 may calculate the average value and standard deviation of the TTP values in the healthy region of the TTP image (for example, the healthy hemisphere shown in FIG. 3A).

A threshold setting unit 54 of the image processing unit 11 sets a threshold based on the standard deviation and average value calculated in step S14 (step S15). For example, the threshold setting unit 54 calculates the threshold by:

$$\text{Threshold}=P_{mean}+2*P_{sd} \quad (1)$$

where $P_{mean}$ represents the average value of pixel values for the healthy region of the perfusion image and $P_{sd}$ represents the standard deviation of the pixel values for the healthy region of the perfusion image.

If the delay image is used as the perfusion image, a threshold is calculated by:

$$\text{Threshold}=D_{mean}+2*D_{sd} \quad (2)$$

where $D_{mean}$ represents the average value of delay times for the healthy region of the delay image and $D_{sd}$ represents the standard deviation of the delay times for the healthy region of the delay image.

The following description will be provided on the assumption that the threshold is calculated by equation (2).

Figure 3B:
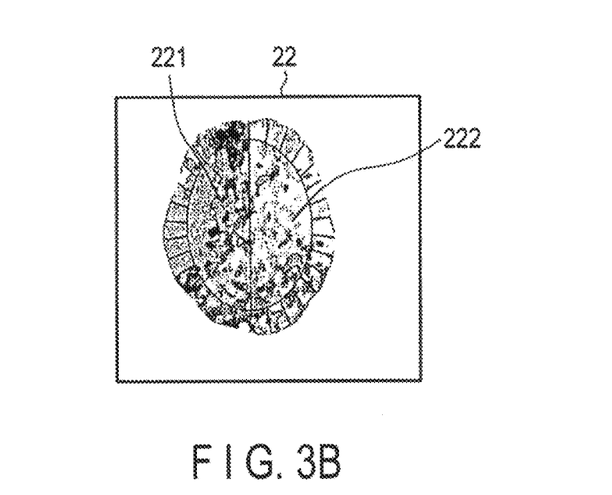
FIG. 3B is a view showing an example of a delay image according to the embodiment.

A lesion candidate region extraction unit 55 of the image processing unit 11 compares the pixel value of each pixel of the perfusion image with the threshold set in step S15, and extracts a lesion candidate region from the perfusion image (step S16). For example, the lesion candidate region extraction unit 55 extracts an image region having a delay time value equal to or larger than the threshold from the lesion hemispheric region of the delay image shown in FIG. 3B. As shown in FIG. 3B, a region having a value exceeding the threshold given by equation (2) is a lesion candidate region 221 which is a collateral circulation candidate or bypass blood vessel candidate. As described above, the lesion candidate region 221 includes a lesion blood vessel candidate and a cerebral parenchyma region nutrified by the lesion blood vessel candidate. The specified lesion candidate region 221 is extracted from the delay image. Data of the lesion candidate region is stored in the storage unit 16.

Finally, a display controller 19 displays the lesion candidate region extracted in step S16 on a display unit 14 (step S17). More specifically, a display image generation unit 56 of the image processing unit 11 performs projection processing for blood vessel volume data to generate a blood vessel image representing the two-dimensional spatial distribution of blood vessels, and superimposes the lesion candidate region on the generated blood vessel image. At this time, the display image generation unit 56 preferably superimposes the lesion candidate region on the blood vessel image after aligning them with each other. The display controller 19 displays the superimposed image on the display unit 14. Note that the display image generation unit 56 may perform projection processing for time-series blood vessel volume data to generate time-series blood vessel images, and superimpose the lesion candidate region on the time-series blood vessel images.

As described above, a medical diagnostic image processing apparatus according to Example 1 extracts a lesion candidate region from a perfusion image, and displays an emphasized imaged in which the lesion candidate region is emphasized. The user can find a collateral circulation or bypass blood vessel by observing the emphasized image. This improves the throughput and efficiency of image diagnosis.

EXAMPLE 2

In Example 2, an application of display of a lesion candidate region extracted in Example 1 will be described. In brief, an image processing unit 11 generates a superimposed image by superimposing the contour of a lesion candidate region on a blood vessel image.

Figure 2B:
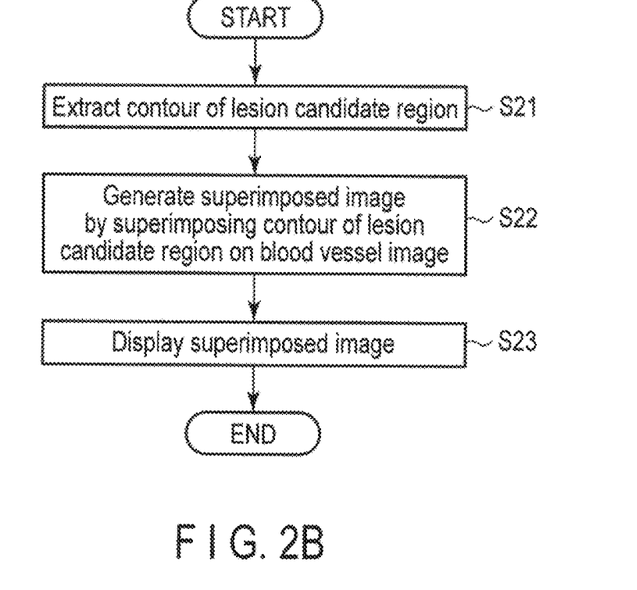
FIG. 2B is a flowchart illustrating a typical processing procedure according to Example 2 of the embodiment.

FIG. 2B is a flowchart illustrating the typical procedure of lesion candidate region display processing according to Example 2.

First, the image processing unit 11 reads out a blood vessel volume data file and a lesion candidate region from a storage unit 16. A contour extraction unit 57 of the image processing unit 11 extracts the contour of the lesion candidate region (step S21).

Figure 4A:
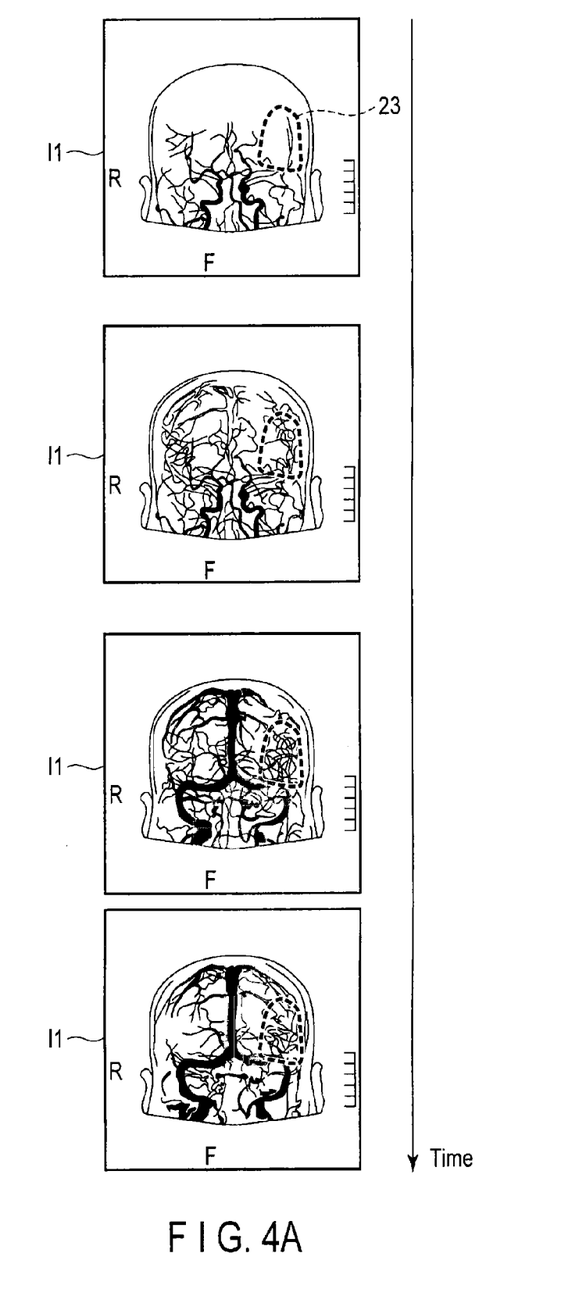
FIG. 4A is a view showing an example of time-series superimposed images generated in step S22 of FIG. 2B.

A display image generation unit 56 of the image processing unit 11 generates a superimposed image by superimposing the contour extracted in step S21 on a blood vessel image (step S22). More specifically, the display image generation unit 56 performs projection processing for the blood vessel volume data to generate a blood vessel image representing the two-dimensional spatial distribution of blood vessels, and superimposes the contour of the lesion candidate region on the generated blood vessel image. At this time, the display image generation unit 56 superimposes the contour on the blood vessel image after aligning them with each other. FIG. 4A is a view showing an example of a superimposed image 11. As shown in FIG. 4A, the superimposed image 11 is combined with a contour 23 of a lesion candidate region.

Finally, a display controller 19 displays the superimposed image generated in step S22 on a display unit 14 (step S23). As shown in FIG. 4A, the superimposed image may be displayed on the display unit 14 in a time-series.

A medical diagnostic image processing apparatus according to Example 2 displays a superimposed image obtained by superimposing the contour of a lesion candidate region on a blood vessel image. When observing the superimposed image, the user can pay attention to the area within the contour of the lesion candidate region, and thus find a collateral circulation or bypass blood vessel more easily. This improves the throughput and efficiency of image diagnosis.

EXAMPLE 3

In Example 3, another application of display of a lesion candidate region extracted in Example 1 will be described. In brief, an image processing unit 11 generates an emphasized image in which a lesion hemispheric region of a blood vessel image is emphasized.

Figure 2C:
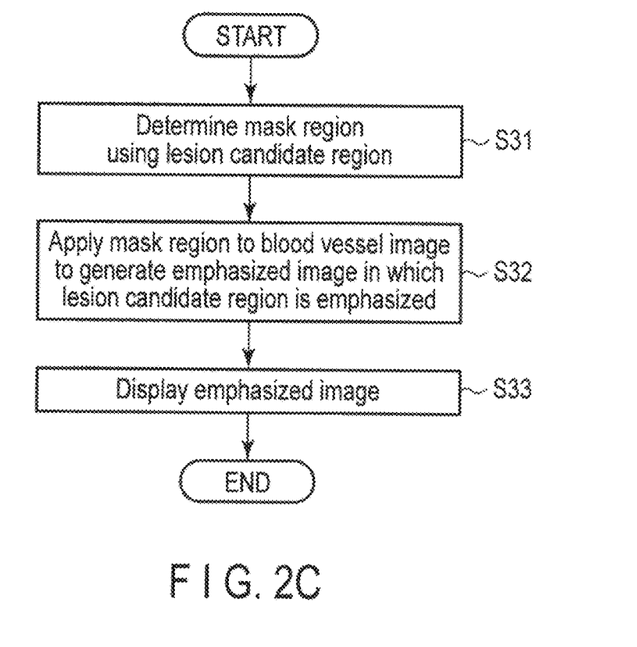
FIG. 2C is a flowchart illustrating a typical processing procedure according to Example 3 of the embodiment.

FIG. 2C is a flowchart illustrating the typical procedure of lesion candidate region display processing according to Example 3.

Figure 4B:
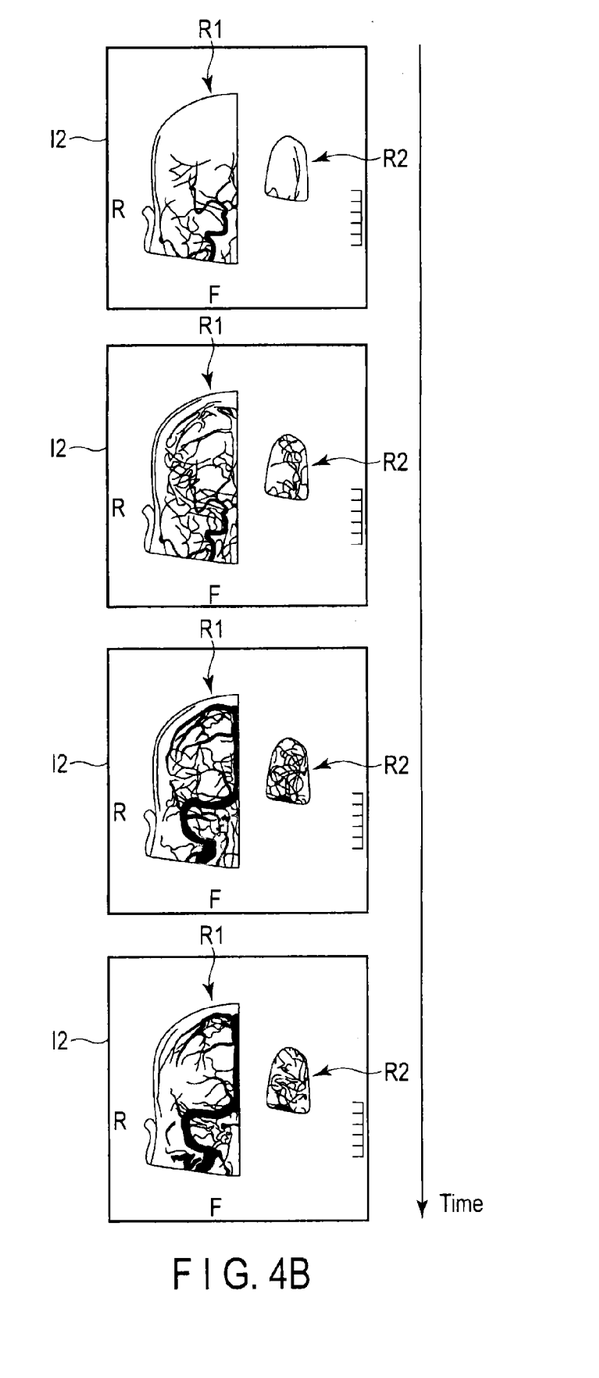
FIG. 4B is a view showing an example of time-series emphasized images generated in step S32 of FIG. 2C.

First, the image processing unit 11 reads out a blood vessel volume data file and a lesion candidate region from a storage unit 16. A mask region determination unit 58 of the image processing unit 11 determines a mask region using the lesion candidate region (step S31). The mask region is defined within the non-display range of the blood vessel volume data file. More specifically, as shown in FIG. 4B, the mask region is set in an image region except for a lesion candidate region 23 of a lesion hemispheric region of the blood vessel volume data file so that only the lesion candidate region 23 is displayed with respect to the lesion hemispheric region. It is not necessary to set the mask region for comparison with respect to a healthy region.

A display image generation unit 56 of the image processing unit 11 applies the mask region determined in step S31 to the blood vessel volume data file, thereby generating an emphasized image in which the lesion candidate region included in the blood vessel volume data file is left, and a region except for the left region has a luminance or brightness lower than that of the left region (step S32). More specifically, the display image generation unit 56 performs projection processing for the blood vessel volume data file applied with the mask, and generates an emphasized image representing the two-dimensional spatial distribution of blood vessels existing in an image region other than the mask region. FIG. 4B is a view showing an example of the emphasized image generated in step S32. As shown in FIG. 4B, an emphasized image 12 includes a healthy region R1 and a lesion hemispheric region R2. In the emphasized image 12, the whole healthy region R1 is extracted but only an image region other than the mask region is extracted from the lesion hemispheric region R2.

A display controller 19 displays the emphasized image generated in step S32 on a display unit 14 (step S33). The user observes the displayed emphasized image.

A medical diagnostic image processing apparatus according to Example 3 excludes a range within which a mask region is applied from an imaging range of an emphasized image. This enables the medical diagnostic image processing apparatus to exclude blood vessel regions existing before and after a lesion candidate region along the projection direction from the imaging range, thereby distinctly extracting the lesion candidate region. The user can, therefore, readily find the lesion candidate region such as a collateral circulation or bypass blood vessel by observing the emphasized image. The medical diagnostic image processing apparatus can also display the lesion candidate region and the healthy region side by side. This allows the user to readily compare the blood vessel running state of the lesion candidate region with that of the healthy region in one image.

Note that the mask region setting range is not limited to the image region other than the lesion candidate region in the lesion hemispheric region. For example, the mask region may be set in an image region other than an image region (a region corresponding to a lesion) within a healthy region corresponding to the lesion hemispheric region. This facilitates comparison between the lesion candidate region 23 in the lesion hemispheric region and the region corresponding to the lesion in the healthy region. If it is not necessary to display a healthy region, the whole healthy region may be set as a mask region. These mask region setting modes can be arbitrarily set through an input unit 13.

EXAMPLE 4

In Example 4, a method of extracting a lesion blood vessel region from a lesion candidate region extracted in Example 1 and a method of displaying the extracted lesion blood vessel region will be described.

Figure 6A:
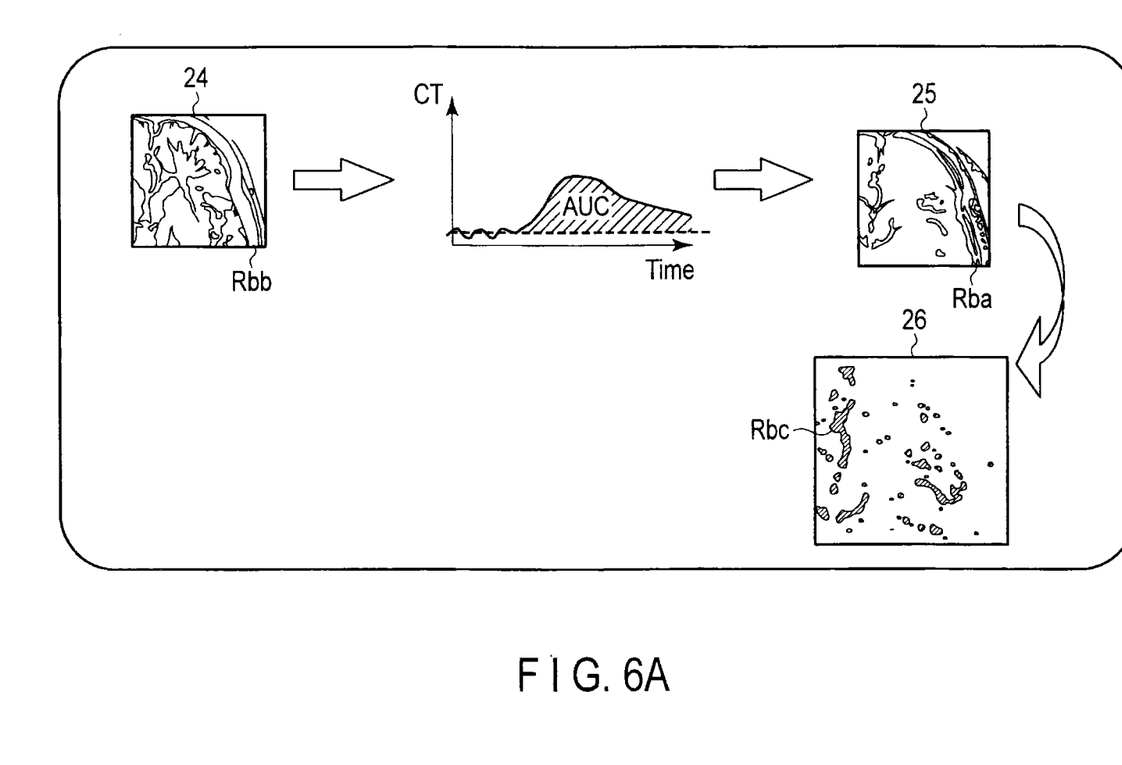
FIG. 6A is a view schematically showing processing according to Example 4 of the embodiment.

First, an image processing unit 11 reads out a blood vessel image and a lesion candidate region from a storage unit 16. A blood vessel region extraction unit 59 of the image processing unit 11 extracts a corresponding region Rbb from a blood vessel image 24 using the lesion candidate region, as shown in FIG. 6A (step S41). The corresponding region Rbb is an image region which is included in the blood vessel image and whose position coincides with that of the lesion candidate region of a perfusion image.

An AUC value calculation unit 60 of the image processing unit 11 calculates an AUC (Area Under the Curve) of each pixel included in the corresponding region Rbb extracted in step S41 (step S42). More specifically, the AUC value calculation unit 60 calculates the time change curve of a CT value for each pixel included in the corresponding region Rbb, as shown in FIG. 6A, and calculates the time integration value (that is, AUC value) of the time change curve. The AUC value is defined by an area bounded by the X- and Y-axes and the time change curve of the CT value.

An AUC image generation unit 61 of the image processing unit 11 generates an AUC image representing the spatial distribution of the AUC values calculated in step S42 (step S43). Alternatively, the AUC image generation unit 61 may generate an AUC image by aligning and adding time-series blood vessel images of all phases.

The blood vessel region extraction unit 59 of the image processing unit 11 extracts a blood vessel region Rba from an AUC image 25 generated in step S43 using the AUC values, as shown in FIG. 6A (step S44). The blood vessel region Rba extracted from the AUC image 25 in step S44 will be referred to as an AUC blood vessel region hereinafter. More specifically, the unit 59 compares the pixel value of each pixel of the AUC image 25 with a predetermined threshold, and extracts a pixel having a pixel value larger than the threshold. A set of a plurality of extracted pixels forms the AUC blood vessel region Rba.

A threshold setting unit 54 of the image processing unit 11 sets a threshold based on the statistic of temporal dynamics of the pixel values of a plurality of pixels included in a healthy region (step S45). More specifically, the threshold setting unit 54 folds the AUC blood vessel region back to the healthy region side with respect to the center line (surface) of the AUC image. The AUC blood vessel region folded back to the healthy region side will be referred to as a folded region hereinafter. The AUC blood vessel region and the folded region have line symmetry with respect to the center line. The threshold setting unit 54 calculates the average value ($T_{mean}$) and standard deviation ($T_{sd}$) of the TTP values shown in FIG. 5 for the folded region. After that, the threshold setting unit 54 calculates a threshold using the calculated average value ($T_{mean}$) 1 and standard deviation ($T_{sd}$) by:

$$\text{Threshold} = T_{mean} 2 * T_{sd} \quad (1)$$

A set of pixels each having a pixel value equal to or larger than the threshold calculated by equation (3) forms a lesion blood vessel region which highly likely includes a collateral circulation or bypass blood vessel.

Figure 2D:
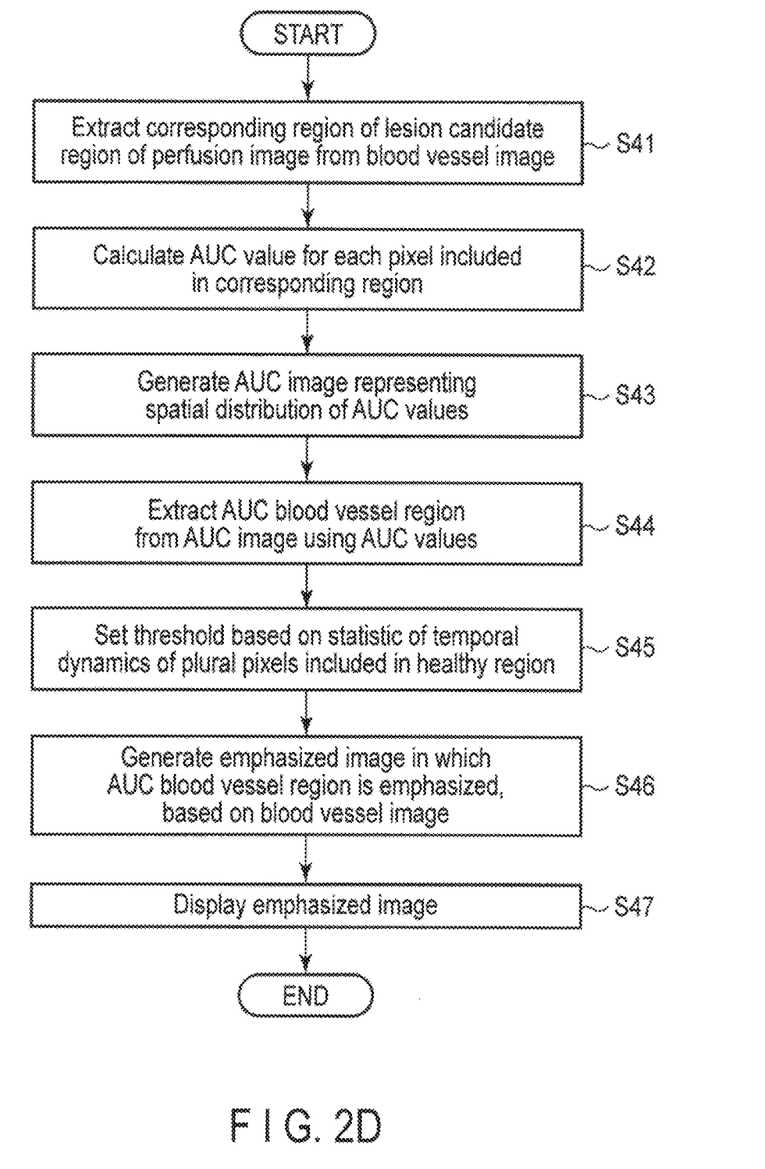
FIG. 2D is a flowchart illustrating a typical processing procedure according to Example 4 of the embodiment.

A lesion blood vessel region extraction unit 62 of the image processing unit 11 compares the pixel value of each pixel of the AUC blood vessel region extracted in step S44 with the threshold set in step S45, and extracts a lesion blood vessel region from the lesion candidate region of the blood vessel image (step S46). More specifically, the unit 62 extracts, as a lesion blood vessel region, pixels each having a pixel value larger than the threshold among a plurality of pixels included in the AUC blood vessel region.

Based on the blood vessel image, a display image generation unit 56 of the image processing unit 11 generates an emphasized image in which the lesion blood vessel region extracted in step S46 is emphasized (step S47). More specifically, the display image generation unit 56 generates an emphasized image 26 by assigning a color value different from another image region to a lesion blood vessel region Rbc of the blood vessel image, as shown in FIG. 6A.

Figure 6B:
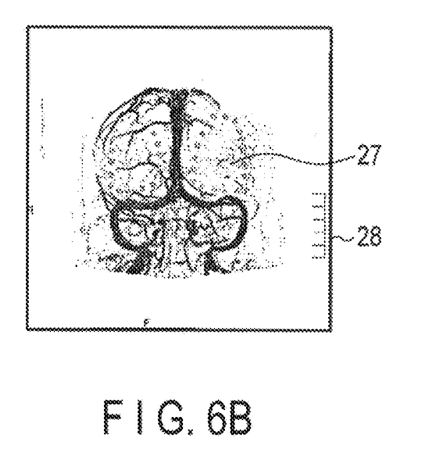
FIG. 6B is a view showing an example of an emphasized image generated in step S47 of FIG. 6A.

Finally, the display controller 19 displays the emphasized image generated in step S47 on the display unit 14 (step S48). The user observes the displayed emphasized image.

A medical diagnostic image processing apparatus according to Example 4 extracts a lesion blood vessel region from a lesion candidate region, and generates an emphasized image in which the extracted lesion blood vessel region is emphasized. The user can readily find a lesion blood vessel such as a collateral circulation or bypass blood vessel by observing the emphasized image.

As described above, the medical diagnostic image processing apparatus according to the embodiment extracts and display a region which highly likely includes a collateral circulation or bypass blood vessel. This enables the user to readily find a collateral circulation or bypass blood vessel.

According to the embodiment, therefore, a medical diagnostic image processing apparatus which can improve the quality of image diagnosis by the user is realized.

The invention claimed is:

1. A medical diagnostic image processing apparatus comprising:
   a processor which executes:
   extracting, from a blood vessel image of a head of a subject, a blood vessel region corresponding to a collateral circulation candidate or a bypass blood vessel candidate included in a perfusion image of the head;
   generating, based on an Area Under the Curve (AUC) value of each pixel of the extracted blood vessel region, an AUC image representing a spatial distribution of the AUC values of the blood vessel region;
   extracting a local blood vessel region from the AUC image based on comparison between the AUC values of the pixels of the AUC image and a preset threshold;
   extracting a lesion blood vessel region from the blood vessel region based on comparison between a pixel value of each pixel of the local blood vessel region and a first threshold which is based on temporal dynamics of a contrast agent in a healthy region included in the AUC image; and
   generating a display image in which the lesion blood vessel region is emphasized based on the blood vessel image; and
   a display which displays the displays image.

2. The medical diagnostic image processing apparatus according to claim 1, wherein the processor further executes:
   extracting a contour of the lesion blood vessel region, and
   generating a superimposed image by superimposing the contour on the blood vessel image, wherein the display displays the superimposed image.

3. The medical diagnostic image processing apparatus according to claim 1, wherein the processor further executes:
   determining a mask region indicating a non-display range based on the lesion blood vessel region, and
   generating, based on the mask region, a display image in which the lesion blood vessel region of the blood vessel image is left, and a remaining region of the blood vessel image has a luminance or brightness lower than that of the left region, wherein the display displays the display image.

4. The medical diagnostic image processing apparatus according to claim 1, wherein the processor further executes:
   extracting a blood vessel region corresponding to a lesion candidate region from the blood vessel image,
   calculating, for each blood vessel portion in the head, a time from when blood flows into a reference portion in the head until the blood flows into the blood vessel portion based on the blood vessel region,
   extracting a lesion blood vessel region as a collateral circulation candidate or a bypass blood vessel candidate from the blood vessel region based on the calculated time, and
   generating a display image in which pixels of the blood vessel image representing the lesion blood vessel region are emphasized, wherein the display displays the display image.

5. The medical diagnostic image processing apparatus according to claim 1, wherein the processor generates the display image by assigning a color value different from an image region except for a third lesion blood vessel region to a pixel representing the third lesion blood vessel region.

6. The medical diagnostic image processing apparatus according to claim 1, wherein a second threshold is set based on pixel values of a healthy region of the perfusion image representing a spatial distribution of blood flow dynamics in the head, and the candidate is extracted from a perfusion image based on comparison between the set second threshold and a pixel value of each pixel of the perfusion image.

7. The medical diagnostic image processing apparatus according to claim 6, wherein the processor further executes:
   dividing the perfusion image into a plurality of regions in correspondence with a plurality of partial regions of the head, calculating a statistic of temporal dynamics with respect to the flow of the contrast agent in each divided partial region of the head based on a perfusion image of the partial region, specifying the healthy region from the plurality of partial regions of the head based on the calculated statistic, calculating an average value and a standard deviation of delay times with respect to the flow of the contrast agent in a region corresponding to the specified healthy region based on a perfusion image of a region corresponding to the healthy region, and setting the first threshold based on the calculated average value and standard deviation.

8. A medical diagnostic image processing apparatus comprising:

a processor which executes:

setting a left region and a right region in a blood vessel image of a head of a subject;

determining, based on a time to peak (TTP) value of each pixel of each of the set left region and the set right region, a first healthy region between the left region and the right region;

specifying a second healthy region corresponding to the determined first healthy region in a delay image representing a spatial distribution of delay times of a contrast agent arriving time from a reference portion of the head;

calculating a statistic of a delay time of each subregion of the second healthy region;

setting a threshold based on the calculated statistic; and determining a lesion candidate region of the delay image based on comparison between the set threshold and a delay time of each subregion of the delay image; and a display which displays the determined lesion candidate region.

9. The medical diagnostic image processing apparatus according to claim 8, wherein the processor executes:

calculating a first statistic of TTP values for each of the left region and the right region; and determining the first healthy region between the left region and the right region based on the calculated first statistic.

10. The medical diagnostic image processing apparatus according to claim 8, wherein the left region is a left hemispheric region of the head, and the right region is a right hemispheric region of the head.

11. The medical diagnostic image processing apparatus according to claim 6, wherein the healthy region is a cerebellar region.

12. The medical diagnostic image processing apparatus according to claim 9, wherein the first statistic is an average value of the TTP values of one of the left region and the right region.

13. The medical diagnostic image processing apparatus according to claim 8, wherein the statistic is an average value and a standard deviation of the delay times.

* * * * *